(12) United States Patent
Watling et al.

(10) Patent No.: US 7,850,906 B2
(45) Date of Patent: *Dec. 14, 2010

(54) METHOD AND APPARATUS FOR VAPOUR PHASE STERILISATION

(75) Inventors: David Watling, Westcott (GB); Anthony Michael Martin, Andover (GB)

(73) Assignee: Bioquell UK Limited, Andover, Hampshire (GB)

( * ) Notice: Subject to any disclaimer, the term of this patent is extended or adjusted under 35 U.S.C. 154(b) by 120 days.

This patent is subject to a terminal disclaimer.

(21) Appl. No.: 11/319,676

(22) Filed: Dec. 28, 2005

(65) Prior Publication Data

US 2006/0099106 A1    May 11, 2006

Related U.S. Application Data

(63) Continuation of application No. 10/088,595, filed as application No. PCT/GB00/03606 on Sep. 20, 2000, now Pat. No. 7,014,813.

(30) Foreign Application Priority Data

Sep. 21, 1999   (GB)   ................................. 9922364.6

(51) Int. Cl.
  *A61L 2/00*   (2006.01)
  *A61L 2/18*   (2006.01)
  *A61L 9/00*   (2006.01)

(52) U.S. Cl. .............................. 422/28; 422/30; 422/31

(58) Field of Classification Search ................... 422/30, 422/28
See application file for complete search history.

(56) References Cited

U.S. PATENT DOCUMENTS 4,512,951 A    4/1985   Koubek 4,797,255 A  *  1/1989   Hatanaka et al. ............... 422/28
4,843,867 A  *  7/1989   Cummings ................. 73/29.03

(Continued)

FOREIGN PATENT DOCUMENTS

EP    0 486 623 B1    1/1997

(Continued)

OTHER PUBLICATIONS

English machne translation of Abstract of JP 04-151098.*

(Continued)

*Primary Examiner*—Sean Conley
*Assistant Examiner*—Regina Yoo
(74) *Attorney, Agent, or Firm*—Workman Nydegger (57) ABSTRACT

An apparatus for sterilizing a sealable enclosure includes a circuit for flow of a sterilizing gas or gasses. The circuit is connected to the enclosure to be sterilized to form a closed circuit and pumps to circulate gas through the circuit and enclosure. The circuit has parallel branches one of which contains apparatus to deactivate a sterilant to be added to the carrier gas flowing through the circuit and apparatus to dehumidify the gas. The other branch contains apparatus to heat the gas and apparatus to supply a sterilant vapor or vapors to the gas. Control apparatus determines which of the parallel branches the gas flows through. The control apparatus maintains flow through one branch passage until the relative humidity falls below a predetermined level. The flow through that branch is then terminated and flow through the other branch initiated.

18 Claims, 2 Drawing Sheets

U.S. PATENT DOCUMENTS

| | | | | |
|---|---|---|---|---|
| 4,898,713 | A | * | 2/1990 | Picard .......................... 422/3 |
| 4,992,247 | A | * | 2/1991 | Foti ............................ 422/304 |
| 5,120,512 | A | * | 6/1992 | Masuda ...................... 422/297 |
| 5,173,258 | A | * | 12/1992 | Childers ...................... 422/27 |
| 5,785,934 | A | | 7/1998 | Jacobs et al. |
| 5,876,664 | A | * | 3/1999 | Childers et al. .............. 422/28 |
| 5,906,794 | A | | 5/1999 | Childers |

FOREIGN PATENT DOCUMENTS

| | | | |
|---|---|---|---|
| EP | 768527 A2 | * | 4/1997 |
| EP | 0 774 263 A1 | | 5/1997 |
| EP | 774263 A1 | * | 5/1997 |
| EP | 0 808 631 A1 | | 11/1997 |
| GB | 2 217 619 A | | 11/1989 |
| GB | 2 308 066 A | | 6/1997 |
| JP | 04151098 A | * | 5/1992 |
| WO | WO 89/06140 | | 7/1989 |
| WO | WO 91/05573 | | 5/1991 |
| WO | WO 97/47331 | | 12/1997 |
| WO | WO 98/57673 | | 12/1998 |
| WO | WO 00/38745 | | 7/2000 |

OTHER PUBLICATIONS

English translation of JP 04-151098.*

P. Swartling et al., *The Sterilizing Effect Against Bacillus subtillis Spores of Hydrogen Peroxide as Different Temperatures and Concentrations*, J. Dairy Res. (1968), 35, 423, pp. 423-438.

Walter C. Schumb et al, *Hydrogen Peroxide*, Reinhold Publishing Corporation, Chapter 8, pp. 447-448 (1968).

* cited by examiner

FIG. 1

METHOD AND APPARATUS FOR VAPOUR PHASE STERILISATION

CROSS-REFERENCE TO RELATED APPLICATIONS

This application is a continuation of U.S. patent application Ser. No. 10/088,595, filed Jun. 11, 2002, now U.S. Pat. No. 7,014,813, which is a US Nationalization of PCT International Application No. PCT/GB00/03606, filed Sep. 20, 2000, which claims priority to United Kingdom Patent Application No. 9922364.4 filed Sep. 21, 1999, which are incorporated herein by reference.

BACKGROUND OF THE INVENTION

1. The Field of the Invention

The present invention relates to methods and apparatus for sterilising the interior of a chamber using either a two component or a multi-component vapour, one component of which will be water.

2. The Relevant Technology and Summary of the Invention

There are numerous applications for sterilising the interior of a chamber including its contents in the pharmaceutical, biotechnology, and food industries, as well as the medical world. A number of compounds have been used as sterilising agents some of which are only partially effective and some of which have serious side effects because they are toxic, corrosive, or can cause other environmental damage. Formaldehyde has long been used as a cheap and quite effective sterilising agent but doubts over its safety and environmental persistence may prevent continued use. Hydrogen peroxide is a simple and cheap compound with good sterilising properties. Its major advantage is that it can be decomposed to water and oxygen, which are totally harmless products. In the vapour phase, hydrogen peroxide can be used to treat work areas of size from safety cabinets to clean rooms. In all gas phase sterilisation, deep layers of contamination will not be effected and good cleaning procedures are necessary as a preliminary to gas phase sterilisation.

Hydrogen peroxide gas sterilisation and decontamination systems have been designed in order to avoid condensation, and as such both flow through and recirculating systems have been so organised as to keep the vapour concentrations, especially of water, below the dew point. Examples of such systems are described in European Patent EP 0486623B1, UK Patent 2217619B, WO89/06140 and UK Patent 2308066A.

More recent work has shown that for rapid surface sterilisation and decontamination in rooms and smaller chambers, or isolators, condensation of a mixture of vapours of a gaseous decontaminant such as hydrogen peroxide and water is essential. It is now believed that gaseous surface sterilisation using hydrogen peroxide is a condensation process so it would seem sensible to examine the process, to see how it may be optimised to take advantage of the condensation process. This knowledge may then be applied not only the sterilisation process using hydrogen peroxide gas but also other mixtures of sterilising gases that rely on condensation for their activity.

In the apparatus described in the European Patent EP 0 486 623 B1 the air/gas mixture is circulated through the sealed chamber to be sterilised and then through the apparatus to produce and control the gas mixture. The gas returning to the apparatus is cleansed of any hydrogen peroxide gas and also dried before more water vapour and hydrogen peroxide gas are added. This cleansing and drying process is likely to be wasteful, as the vapours removed from the circulating gas must be replaced so that condensation may occur in the sealed chamber. The only reason for the removal of these vapours would be if the concentration of the hydrogen peroxide gas had been reduced because of decomposition.

It is now well understood that vapour phase decomposition does not occur at room temperatures, such homogenous decomposition only happens at elevated temperatures as reported in Hydrogen Peroxide, WALTER C. SCHUMB, CHARLES N. SATTERFIELD, RALPH L. WENTWORTH, AMERICAN CHEMICAL. Society, Monograph Series, Catalog Card Number 55-7807, Chapter 8. Decomposition does however happen on surfaces, which are catalytic, but this appears to be very small amounts. To date no observer has seen a measurable increase in oxygen concentration, and the measured hydrogen peroxide gas concentrations conform very closely to the saturated vapour pressures of the original aqueous solution that is evaporated into the air stream. All of the indications are therefore that the amount of vapour phase decomposition of hydrogen peroxide is very small.

Since this sterilisation process relies on condensation of the hydrogen peroxide vapour then the most critical parameter is the rate at which this condensation may be achieved. The amount of hydrogen peroxide vapour available for condensation within the sealed enclosure will depend on the vapour concentration delivered to the chamber and the concentration leaving the chamber. The difference between these two amounts will be the quantity of hydrogen peroxide that is available to form a film of condensation.

The maximum concentration of vapour that can be delivered to the chamber depends on the temperature of the gas stream entering the chamber, the concentration of the aqueous sterilising solution being evaporated into the gas stream and the total water content of the gas. The carrier gas, normally air, that is used to transport the sterilising vapours through the total system will never be perfectly dry, even after passing through the drying system. This additional water in the carrier gas will dilute the hydrogen peroxide to a small extent and this additional water will reduce the amount of hydrogen peroxide that may be carried by the gas. The concentration of the vapour leaving the sealed chamber, once stable conditions have been reached, will be determined by the saturated vapour pressure for the conditions at the exit of the sealed chamber. Thus, if it is assumed that only insignificant amounts of decomposition occur, then the rate of condensation will depend on the concentration of the gases delivered to the chamber and the temperature of the gases leaving the chamber.

In general there are two factors that are important when considering a gaseous surface sterilisation process. The first and most important is to be sure that the process has been successful and the second is to achieve sterilisation in the minimum possible time. The most common technique for assuring sterility is to develop a cycle and to test the performance with biological indicators. This cycle development will include optimisation of each phase of the sterilisation cycle. This is a complex issue as there are many parameters to be considered during the optimisation process apart from the obvious considerations of gas concentration and flow. Some of the less obvious ones are the starting value of the relative humidity, the moisture content of any microorganism, the rate of condensation, and the length of time it may take for the condensate to kill any microorganism. The technique used for the removal of the sterilant gas at the end of the cycle will also have marked influence on the total cycle time.

The optimised cycle then becomes fixed using the same physical parameters such as flow rates, times etc., but does not take into account any external factors that may change, e.g., the external temperature which will have an influence on the effectiveness of the cycle.

The problem with this fixed technique is that if some external influences change which have not been taken into consideration during the cycle development then a cycle, although properly developed, may become unsuccessful. The best method to overcome this difficulty is to measure those parameters that actually cause the sterilisation and use these measurements to control the cycle, rather than to use a set of predetermined factors to run identical cycles. The technique of using the measurements to control the cycle will lead to changes in the details of the cycle to counteract any changes in the circumstances surrounding the process.

This procedure also has the advantage of ensuring the minimum reliable cycle time, since the process will progress to a point where it is effective and no further. It is not necessary to add large safety margins to the cycle to ensure that it is effective, as the point at which it is effective is known from the measurements.

The objects of the present invention are to control the sterilisation cycle using sensors, and to provide a recirculating system that does not require the steps of removing water vapour and sterilising gas mixtures during the critical sterilisation phase of the cycle.

This invention provides a method of sterilising a sealable enclosure comprising the steps of initially reducing the relative humidity in the enclosure to about 30 to 40%, circulating a carrier gas to the enclosure, raising the temperature of the circulating gas above ambient, supplying a sterilant vapour or vapours to the circulating carrier gas sufficient to saturate substantially the gas whereby on cooling in the enclosure, a condensate of the sterilant vapour is formed on surfaces in the enclosure, distributing the gas/vapour throughout the enclosure to ensure that the condensate is formed on all surfaces in the enclosure, measuring the amount of condensate formed on a surface of the enclosure and continuing to circulate the gas/vapour until a required amount of condensate has formed in the enclosure terminating supply of sterilant vapour to the gas whilst continuing to circulate the saturated gas/vapour to maintain the condensate on the surface for a predetermined period of time and finally extracting the sterilant vapour from the carrier gas whilst continuing to circulate the carrier gas through the enclosure to extract the condensate from the enclosure.

Preferably the sterilant vapour is extracted from the carrier gas by breaking down the vapour into disposable constituents.

It is also preferred that the sterilant vapour is hydrogen peroxide and water vapour. In this case the hydrogen peroxide extracted from the chamber with the circulating gas is subjected to catalytic action to break the hydrogen peroxide down into water vapour and oxygen, the former being extracted from the gas before the gas is recirculated through the enclosure.

The initial step of reducing the relative humidity in the enclosure may be carried out by circulating the carrier gas through the chamber and extracting water vapour from the circulating gas outside the chamber.

The relative humidity in the enclosure may be reduced initially to about 35%. In addition, the enclosure may be held at said reduced relative humidity for a period of time according to the size of enclosure and flow rate of gas to ensure dryness of said surfaces in the enclosure.

The invention also provides a method of sterilising a sealable enclosure comprising the steps of circulating a carrier gas through the enclosure and through a flow path having an inlet to the enclosure and an outlet from the enclosure, the flow path having parallel branches in one of which any sterilant in the gas flow is rendered suitable for disposal and any water vapour content in the gas is reduced and the other of which the carrier gas is heated and sterilant is added to the gas, the method further comprising the steps of initially circulating said carrier gas through said one branch, monitoring the moisture content of the gas in the enclosure and terminating flow of carrier gas through said one branch when the relative humidity in the enclosure has been reduced to a predetermined level such that the surfaces of the enclosure are relatively dry, initiating flow of the carrier gas through said other branch and adding a sterilant vapour or vapours to the gas passing through the other branch until condensation of the sterilant takes place in the enclosure, terminating supply of sterilant to the carrier gas, continuing to circulate the carrier gas substantially saturated with sterilant vapour for a predetermined time to ensure sterilisation of the enclosure terminating flow through said other branch and redirecting the flow of carrier gas through said one branch to extract the sterilant from the gas enclosure to render the sterilant suitable for disposal and to reduce the relative humidity of the carrier gas.

Entry to one branch is closed and entry to the other branch may be opened and vice versa to provide flow through one or other of the branches. For example, valve means may permit flow into one branch and not the other and vice versa.

Alternatively, pump means may be provided in said parallel branches and are used to cause gas flow along one or other of the parallel branches in the flow path.

The invention also provides an apparatus for sterilising a sealable enclosure comprising a circuit for flow of carrier gases in which the enclosure to be sterilised may be connected to form a closed circuit with the enclosure, means for causing a carrier gas to circulate through the circuit including the enclosure, means to remove water vapour from the circulating gas to dry the enclosure and surfaces thereof, means to raise the temperature of the circulating gas above ambient, means to supply a sterilant vapour or vapours to the circulating gas to form, on cooling in the enclosure, a condensate on the surfaces in the enclosure, means to distribute the gas/vapours throughout the enclosure to ensure that the condensate is formed on all surfaces in the enclosure, means to measure the amount of condensate formed on a surface of the enclosure and to terminate the supply of sterilant vapour to the carrier gas when the required level of condensate has formed, the circulation of carrier gas continuing to extract condensate from the enclosure.

The invention further provides an apparatus for sterilising a sealable enclosure comprising a circuit for flow of a gas or gasses, the circuit having means to receive and connect an enclosure to be sterilised in the circuit to form a closed circuit therewith, means to circulate gas through the circuit and enclosure, and having parallel branches in the circuit one of which contains means to deactivate a sterilant to be added to the carrier gas flowing through the circuit and means to dehumidify the gas and the other of which branches contains means to heat the gas and means to supply a sterilant vapour or vapours to the gas, the apparatus further comprising control means for determining through which of the parallel branches the gas flows, the control means including means to determine the relative humidity of the gas exiting the enclosure to maintain said one branch passage open until the relative humidity falls below a predetermined level and then to close that branch and to open the other branch and means to measure condensation in the enclosure to close said other branch and to open said one branch when the required amount of condensation has built up in the enclosure.

It has been found that in aqueous solutions of hydrogen peroxide very fast kill rates are achieved even at 10% hydrogen peroxide concentrations with even faster kills at 20% solution. Since we believe that gaseous surface sterilisation is a micro condensation process, then it may be considered to be analogous to the work described in the publication by THE STERILISING EFFECT AGAINST BACILLUS SUBTILIS SPORES OF HYDROGEN PEROXIDE AT DIFFERENT TEMPERATURES AND CONCENTRATIONS; P. Swartling and B. LINDGREN J. DAIRY RES. (1968), 35,423. This gives a good guide as to the expected results that may be achieved with a gaseous condensation process.

This also suggests that should some small amount of decomposition occur because of surface catalysation of the gas then kills would still be achieved. In reality such decomposition appears to be very small indeed as indicated by the gas concentration data.

BRIEF DESCRIPTION OF THE DRAWINGS

The following is a description of some specific embodiments of the invention, reference being made to the accompanying drawings in which.

DETAILED DESCRIPTION OF THE PREFERRED EMBODIMENTS

Figure 1:
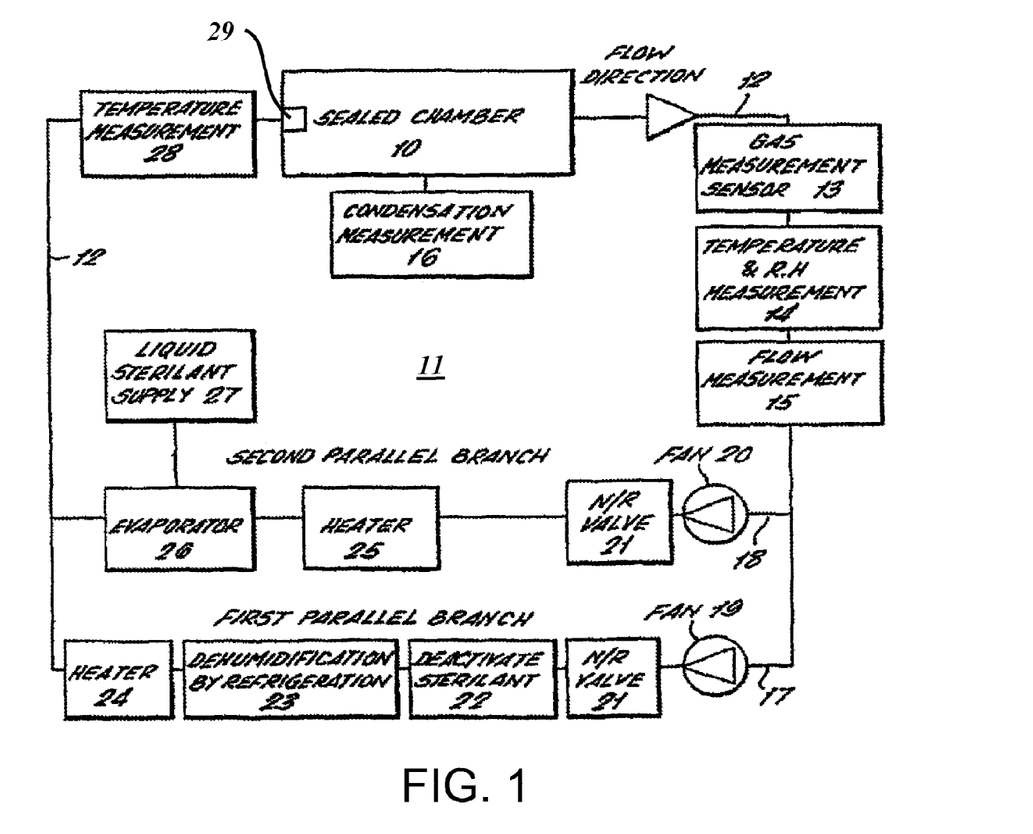
FIG. 1 is a diagrammatic view of a sealed chamber and a sterilisation circuit connected to the chamber for sterilising the interior and contents of the chamber using a gas carrying an aqueous vapour of a liquid sterilant, the circuit having two pumps or fans.

The apparatus comprises a sealed chamber 10, and an apparatus included generally at 11 incorporating a dual circuit for dehumidification, sterilising and aeration of the sealed chamber 10. A carrier gas, i.e., air, and a sterilising gas or gases are drawn from the sealed chamber to the apparatus through sealed connections fluidly connecting the chamber to the apparatus.

The apparatus comprises a gas flow circuit 12 containing in series, a gas monitor 13 a temperature and humidity monitor 14 and a flow measurement device 15. The gas monitor is an electrochemical cell giving a signal proportional to the gas concentration or can be a near infra-red spectrophotometer. Suitable temperature and humidity sensors 14 are commonly available as a single commercial instrument, and any such device that is resistant to hydrogen peroxide vapour would be suitable for this application. The most suitable, and cost effective, flow measurement 15 system is based on the measurement of the pressure difference across a restriction in the flow, typically an orifice plate.

Attached to the sealed chamber is a condensation measurement system 16. Proprietary systems are not readily available, but techniques have been developed that rely on the change in reflectivity of a surface in the chamber to indicate the mass of condensate that has formed. Alternative techniques that may include measuring equipment may be mounted on the outside of the chamber.

Downstream of the flow measurement system the circuit divides into two parallel branches 17, 18. Each branch has a fan 19, 20 and each fan has an associated non-return valve 21. As the pressure required to force the circulating gas round the system is generally not large then a standard variable speed centrifugal fan would suffice for such an application. The non-return valves are required to ensure that there is no back flow in the wrong direction. Simple flap devices are all that is required in this application. In the first parallel branch 17 is a system 22 to deactivate and remove the sterilant gas or gases from the carrier gas, and a further system 23 to dehumidify the gas stream. Downstream of the dehumidification system is a heater 24 to raise the circulating gas temperature. The deactivating system for the sterilant gas comprises a catalyst bed, which decomposes the vapour to harmless components. For hydrogen peroxide gas a suitable catalyst would be ruthenium on inert pellets which decomposes the gas to water vapour and oxygen.

A desiccant dryer may perform the dehumidification process, but a more suitable technique would be to reduce the gas temperature using a refrigeration system. The reduction in temperature causes the water vapour to condense with the products of decomposition. The resulting condensate and decomposition products may then be pumped away. It is necessary to raise the circulating gas temperature after dehumidification and an electric heater 24 or other heating means is placed downstream of the dehumidifier for the purpose.

In the second parallel branch is a heater 25 to raise the gas temperature prior to entering an evaporator 26, in which the liquid sterilant is turned to vapour by heating. A liquid sterilant supply 27 controls the liquid flow to the evaporator.

The heater 25 may be of a similar construction to the other heater 24. The evaporator is a flash evaporator in which the liquid sterilant is evaporated by dropping under gravity a stream of liquid onto a heated surface. The flow of liquid from the sterilant supply is fed onto the heated surface at a selected rate by using a variable speed pump, which is controlled from a flow measuring system. The gas temperature entering the sealed chamber 10 is measured at 28 using a standard temperature probe.

Gas entry to the chamber 10 is through a gas distribution system 29 including a rotating nozzle arrangement which projects gas at high temperature and velocity to every part of the chamber. In addition a system for control gas pressure in the circuit to raise or reduce pressure as required is provided.

Figure 2:
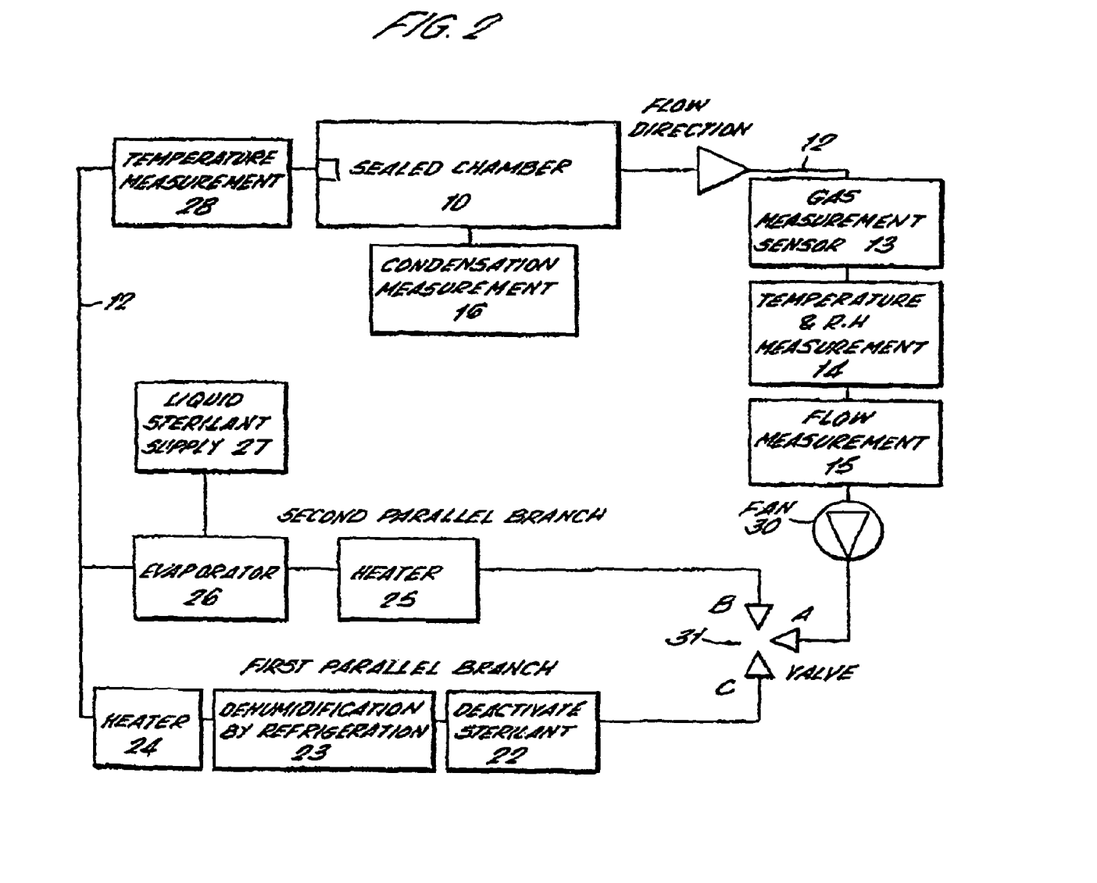
FIG. 2 is a diagrammatic view of a sealed chamber and a further form of circuit connected to the chamber for sterilisation of the interior of the chamber and its contents using a gas containing an aqueous vapour of a liquid sterilant, the circuit having a single pump or fan.

The components in the alternative arrangement shown in FIG. 2 are the same, with the same numbering except for the fan and valve arrangement. In FIG. 2 the gas or gases are driven round the system by a single fan of pump 30. The gas or gas mixtures leaving the fan or pump pass to a three way valve 31, which diverts the flow either to the first parallel branch by connecting port A to port C, or to the second parallel branch by connecting port A to port B. The valve is typically an electrically driven three-way ball valve.

The method of sterilising the enclosure using the above apparatus comprises the steps of reducing the relative humidity in the enclosure, then circulating a carrier gas containing an aqueous vapour of the sterilising gas or gases, and finally removing the sterilising gas or gases.

The first phase of reducing the relative humidity is essential to ensure that all of the surfaces inside the sealable chamber are at the same state of dryness. During the second phase the sterilising gas or gases are delivered to the sealed chamber at an elevated temperature in order that as much as possible of the sterilant may be transported into the sealed chamber. The third and final stage is the removal of the sterilant gas or gases by passing clean dry carrier gas into the sealed chamber to carry away the active gas or gases.

The first phase of reducing the humidity may be in two parts, the first to reduce the relative humidity to a pre-selected value, and a second part to hold the humidity at that value to allow the sealed chamber to come to a stable state.

Similarly the second phase when the gas or gases are passed into the sealed chamber is in two parts. The first part is to raise the concentration and generate the required level of condensation on the surfaces, with a second dwell part to allow the condensate to act on the microorganisms. The level of condensation is measured during the first part of the second phase and when it has reached the required level the supply of sterilising gas or gases is stopped but the carrier gas with the associated saturated vapours continues to circulate. The circulating saturated vapour prevents evaporation of the layer of condensation allowing the liquid film to act on the microorganisms.

During the third and final phase of the sterilisation cycle the carrier gas together with the sterilising gas or gases is circulated through a system to render the active gases harmless, so that it may be taken away, whilst at the same time removing the water vapour in a dehumidifier. The clean carrier gas is then returned to the sealed chamber where it gathers more of the active gas or gases thus further reducing to the level of the active ingredients. This process continues until the active ingredients have been reduced to an acceptable level.

1. The relative humidity (RH) must be controlled at the start of the sterilisation cycle. We have established that the optimum value is between 30 and 40%. There are two points to be considered about the starting value of RH, the first is to obtain the shortest possible cycle (this requires the RH to be reduced to about 35%), and the second is to achieve a repeatable cycle. The repeatability depends on using the same starting value of RH and this may well have to be higher than 35% depending on local conditions. As it may not always be practical to achieve a starting value of 35% for the RH then it is essential that the same starting value is always used. Higher values of RH will increase the time required to achieve sterilisation as the condensate forming on surfaces will be diluted by any water that is present.

2. The amount of condensation is important, too much and the time to remove the surface layer after sterilisation has been achieved will be increased, as it would take longer to dry the surfaces. If insufficient condensation is allowed to form then sterilisation will not take place. The accurate measurement of this surface layer is essential to the process.

3. From the work of Swartling et al referred to above, it is clear that some "soaking" time will be required for the condensed liquid to be effective. This is built into the sterilisation cycle as a dwell period, a safety margin should be allowed within this dwell period to ensure that a total kill has been achieved. This period will normally be no more than a few minutes including the safety margin.

4. The distribution of the hot gas entering the chamber is also important. As the gas enters the chamber it will rapidly start to cool and form condensation. If the gas is not thoroughly mixed as it enters the chamber then there will be sites of preferential condensation. If this should happen then it follows that other areas within the chamber will have less condensation, and to achieve a total kill in all areas an excess of gas will be required. This excess will be unevenly distributed and also take longer to remove at the end of the cycle when it is required to return the chamber to normal use.

5. The measurement of the concentration and temperature of the gas leaving the chamber tells the system that saturated vapour pressure has been reached. Whilst this is not a critical parameter it does indicate that condensation will form. If the concentration is too low and condensation does not form then the cycle should be aborted and these measurements will confirm that action.

Thus the process cycle comprises the following steps:

1. The chamber is brought to a starting value of RH, normally 35%. The chamber should be held at this level for a few minutes to ensure all of the surfaces have been brought to equilibrium.

2. Sterilising gas or gases and water vapour are passed into the chamber at an elevated temperature and distributed so as to generate an even layer of condensation. The amount of condensation is measured and when it has reached a sufficient value the gas and water vapour generator is switched off.

3. The condensed gas or gases and water remain on the surfaces for a sufficient length of time to cause sterilisation.

4. At the end of the dwell period the chamber is fed with clean dry air, which causes the surface condensation to evaporate and is therefore cleared from the chamber.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for sterilising a sealable enclosure comprising circulating a carrier gas in a closed loop fashion through the enclosure and through a flow path having an inlet to the enclosure and an outlet from the enclosure, the method further comprising:
    initiating flow of a carrier gas along the flow path and through the enclosure,
    adding a sterilant vapour or vapours to the gas passing through the flow path until condensation of the sterilant takes place in the enclosure,
    terminating supply of the sterilant vapour or vapours to the carrier gas whilst continuing to circulate the gas for a predetermined period of time through the flow path and through the enclosure without extracting the sterilant vapour from the gas to ensure sterilisation of the enclosure and then extracting sterilant from the circulating gas and rendering the sterilant suitable for disposal and reducing a relative humidity of the circulating gas;
    wherein the flow path has a pair of parallel branches comprising a first branch and a second branch, the first and second branches being configured to provide alternate flow paths for circulating the carrier gas through the enclosure such that when the first branch is opened the second branch is closed and vice versa, wherein:
    the sterilant vapour is added to the circulating carrier gas in the first branch when the first branch is opened and the second branch is closed; and
    the sterilant vapour is extracted from the circulating carrier gas in the second branch when the second branch is opened and the first branch is closed.

2. A method as claimed in claim 1, wherein the sterilant vapour is extracted from the circulating carrier gas by breaking down the vapour into disposable constituents.

3. A method as claimed in claim 1, wherein the sterilant vapour is hydrogen peroxide and water vapour.

4. A method as claimed in claim 3, wherein the hydrogen peroxide extracted from the enclosure with the circulating gas is subjected to catalytic action to break the hydrogen peroxide down into water vapour and oxygen, the former being extracted from the gas before the gas is recirculated through the enclosure.

5. A method as claimed in claim 1, wherein the step of reducing the relative humidity in the enclosure is carried out by circulating the carrier gas through the chamber and extracting water vapour from the circulating gas outside the chamber.

6. A method as claimed in claim 1, wherein the relative humidity in the enclosure is reduced to about 35%.

7. A method as claimed in claim 1, wherein following said reduction in relative humidity in the enclosure, said reduced relative humidity is maintained for a period of time according to the size of enclosure and flow rate of gas to ensure dryness of the enclosure.

8. A method as claimed in claim 1, wherein condensation of the sterilant is maintained in the enclosure for a predetermined period of time to ensure sterilisation of the enclosure.

9. A method as claimed in claim 1, wherein the flow path from said outlet divides to provide two flow paths to the pair of parallel branches and the parallel branches reunite to form one flow path leading to the inlet.

10. A method of sterilising a sealable enclosure comprising the steps of:
 initially reducing the relative humidity in the enclosure to about 30 to 40%;
 circulating a carrier gas through the enclosure;
 raising the temperature of the circulating carrier gas above ambient;
 supplying a sterilant vapour or vapours to the circulating carrier gas sufficient to saturate substantially the gas whereby on cooling in the enclosure, a condensate of the sterilant vapour is formed on surfaces in the enclosure;
 distributing the saturated carrier gas throughout the enclosure to ensure that the condensate is formed on all surfaces in the enclosure;
 measuring the amount of condensate formed on a surface of the enclosure and continuing to circulate the saturated carrier gas until a required amount of condensate has formed in the enclosure;
 terminating supply of sterilant vapour to the circulating carrier gas whilst continuing to circulate the saturated carrier gas to maintain the condensate on the surface for a predetermined period of time; and
 finally extracting the sterilant vapour from the carrier gas whilst continuing to circulate the carrier gas through the enclosure to extract the condensate from the enclosure.

11. A method as claimed in claim 10, wherein the sterilant vapour is extracted from the carrier gas by breaking down the vapour into disposable constituents.

12. A method as claimed in claim 10, wherein the sterilant vapour is hydrogen peroxide and water vapour.

13. A method as claimed in claim 12, wherein the hydrogen peroxide extracted from the enclosure with the circulating carrier gas is subjected to catalytic action to break the hydrogen peroxide down into water vapour and oxygen, the former being extracted from the gas before the gas is recirculated through the enclosure.

14. A method as claimed in claim 10, wherein the initial step of reducing the relative humidity in the enclosure is carried out by circulating the carrier gas through the enclosure and extracting water vapour from the circulating gas outside the enclosure.

15. A method as claimed in claim 10, wherein the relative humidity in the enclosure is reduced to about 35%.

16. A method as claimed in claim 10, wherein following said reduction in relative humidity in the enclosure, said reduced relative humidity is maintained for a period of time according to the size of the enclosure and flow rate of gas to ensure dryness of said surfaces in the enclosure.

17. A method as claimed in claim 10, wherein condensation of the sterilant is maintained on the surfaces within the enclosure for a predetermined period of time to ensure sterilisation of the surfaces.

18. A method for sterilizing a sealable enclosure using a flow path external to the sealable enclosure to circulate a carrier gas through the enclosure in a closed loop fashion, the flow path having a pair of parallel branches comprising a first branch and a second branch that provide alternate flow paths for circulating the carrier gas through the enclosure, the method comprising:
 initiating a circulating flow of a carrier gas through the first branch of the flow path and through the enclosure in a closed loop fashion while preventing the carrier gas from flowing through the second branch of the flow path;
 adding a sterilant vapor to the circulating carrier gas in the first branch of the flow path so that the sterilant vapor circulates with the carrier gas through the enclosure and through the first branch of the flow path in a closed loop fashion while the carrier gas continues to be prevented from flowing through the second branch of the flow path, the sterilant vapor being continually added to the circulating vapor/gas mixture as it circulates through the first branch of the flow path until condensation of the sterilant takes place in the enclosure;
 monitoring the moisture content of the vapor/gas mixture in the enclosure;
 terminating supply of the sterilant vapor to the circulating vapor/gas mixture while continuing to circulate the vapor/gas mixture through the enclosure and through the flow path in a closed loop fashion for a predetermined period of time without extracting the sterilant from the vapor/gas mixture;
 circulating the vapor/gas mixture through the second branch of the flow path and through the enclosure in a closed loop fashion while preventing the vapor/gas mixture from flowing through the first branch of the flow path; and
 extracting sterilant from the circulating vapor/gas mixture in the second branch of the flow path and reducing a relative humidity of the circulating carrier gas in the second branch of the flow path while continuing to circulate the vapor/gas mixture through the enclosure and through the second branch of the flow path in a closed loop fashion and rendering the sterilant suitable for disposal while the carrier gas continues to be prevented from flowing through the first branch of the flow path.

* * * * *

UNITED STATES PATENT AND TRADEMARK OFFICE
CERTIFICATE OF CORRECTION

| | |
|---|---|
| PATENT NO. | : 7,850,906 B2 |
| APPLICATION NO. | : 11/319676 |
| DATED | : December 14, 2010 |
| INVENTOR(S) | : Watling et al. |

It is certified that error appears in the above-identified patent and that said Letters Patent is hereby corrected as shown below:

Drawings
Delete Drawing Sheet 2 and replace with attached Drawing Sheet 2 in which the "apparatus" has been labeled with --11--

Column 1
Line 56, after "only" insert --to--
Line 57, before "other" insert --to--

Column 2
Line 10, change "AMERICAN CHEMICAL. Society," to --American Chemical Society,--
Line 65, before "marked" insert --a--

Column 3
Line 39, after "enclosure" insert --,--

Column 4
Line 17, after "enclosure" insert --,--

Column 5
Line 46, change "gas monitor 13" to --gas monitor 13,--
Line 47, change "14" to --14,--

Column 7
Line 38, change "too much and" to --if too much is formed,--

Signed and Sealed this
Twenty-first Day of June, 2011

David J. Kappos
*Director of the United States Patent and Trademark Office*